(12) United States Patent
Jones (10) Patent No.: US 11,489,696 B2
(45) Date of Patent: Nov. 1, 2022

(54) SURGICAL INSTRUMENT WITH SINGLE WIRE DIGITAL COMMUNICATION OVER DIFFERENTIAL BUS

(71) Applicant: Covidien LP, Mansfield, MA (US)

(72) Inventor: Travis Jones, Erie, CO (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 17/084,171

(22) Filed: Oct. 29, 2020

(65) Prior Publication Data

US 2021/0184891 A1     Jun. 17, 2021

Related U.S. Application Data

(60) Provisional application No. 62/948,996, filed on Dec. 17, 2019.

(51) Int. Cl.
    *H04L 12/40*     (2006.01)
    *H04B 1/40*      (2015.01)

(52) U.S. Cl.
    CPC ......... *H04L 12/40143* (2013.01); *H04B 1/40* (2013.01)

(58) Field of Classification Search
    CPC ............................ B04B 1/40; H04L 12/40143
    See application file for complete search history.

(56) References Cited

U.S. PATENT DOCUMENTS

| | | | |
|---|---|---|---|
| 5,206,905 A | 4/1993 | Lee et al. | |
| 9,168,054 B2 * | 10/2015 | Turner | .................. H03M 11/24 |
| 9,439,668 B2 | 9/2016 | Timm et al. | |
| 10,117,702 B2 | 11/2018 | Danziger et al. | |
| 10,194,973 B2 | 2/2019 | Wiener et al. | |
| 10,278,862 B2 | 5/2019 | Wysopal | |
| 10,303,641 B2 | 5/2019 | Collins et al. | |

(Continued)

FOREIGN PATENT DOCUMENTS

| | | |
|---|---|---|
| AU | 2010303385 A1 | 5/2012 |
| CN | 102665585 A | 9/2012 |

(Continued)

OTHER PUBLICATIONS

Extended European Search Report issued in corresponding application EP 20213701.4 dated May 3, 2021 (7 pages).

*Primary Examiner* — Sung S Ahn
(74) *Attorney, Agent, or Firm* — Carter, DeLuca & Farrell LLP (57) ABSTRACT

A single wire digital communication system for use with an ultrasonic surgical instrument and an ultrasonic surgical instrument including a single wire digital communication system. The single wire digital communication system includes first transmitter logic buffer and first receiver logic buffer operably coupled to a first single wire device via a first single wire communication bus. The single wire digital communication system also includes a first differential transceiver operational amplifier operably coupled to the first transmitter logic buffer via a first transmitter signal line and operably coupled to the first receiver logic buffer via a first receiver signal line. A second differential transceiver operational amplifier is operably coupled to the first differential transceiver operational amplifier via at least one differential bus. A second single wire device is operably coupled to the differential bus and configured to communicate with the first single wire device.

20 Claims, 7 Drawing Sheets

(56) References Cited

U.S. PATENT DOCUMENTS

2005/0258865 A1\* 11/2005 Behrendt .................. H04L 5/14
  326/82
2015/0148830 A1\* 5/2015 Stulen ............ A61B 17/320068
  606/169

FOREIGN PATENT DOCUMENTS

| CN | 102854253 B | 10/2014 |
|---|---|---|
| CN | 104363849 B | 5/2018 |
| EP | 1997438 A2 | 12/2008 |
| FR | 2929780 A1 | 10/2009 |
| WO | 2014197479 A2 | 12/2014 |
| WO | 2015077138 A2 | 5/2015 |
| WO | 2015155242 A1 | 10/2015 |
| WO | 2019079378 A1 | 4/2019 |

\* cited by examiner

SURGICAL INSTRUMENT WITH SINGLE WIRE DIGITAL COMMUNICATION OVER DIFFERENTIAL BUS

CROSS-REFERENCE TO RELATED APPLICATIONS

This application claims the benefit of and priority to U.S. Provisional Patent Application Ser. No. 62/948,996 filed Dec. 17, 2019, the entire disclosure of which is incorporated by reference herein.

FIELD

The present disclosure relates to ultrasonic surgical instruments and, more particularly, to a communication protocol for a surgical instrument in which data is communicated through a bus, the protocol eliminating the need for multiple buses for transmitting information between various components in the system.

BACKGROUND

Ultrasonic surgical instruments utilize ultrasonic energy, i.e., ultrasonic vibrations, to treat tissue. More specifically, ultrasonic surgical instruments utilize mechanical vibration energy transmitted at ultrasonic frequencies to coagulate, cauterize, fuse, seal, cut, desiccate, and/or fulgurate tissue to affect hemostasis.

Ultrasonic surgical instruments typically employ a transducer coupled to a handle of the ultrasonic surgical instrument and configured to produce ultrasonic energy for transmission along a waveguide to an end effector of the ultrasonic surgical instrument that is designed to treat tissue with the ultrasonic energy. The transducer may be driven by an ultrasonic generator that is on-board, e.g., on or within the handle of the ultrasonic surgical instrument, or remotely disposed, e.g., as a set-top box connected to the ultrasonic surgical instrument via a surgical cable. The end effector of the ultrasonic surgical instrument may include a blade that receives the ultrasonic energy from the waveguide for application to tissue and a jaw member configured to clamp tissue between the blade and the jaw member to facilitate treatment thereof.

SUMMARY

Various components of electrosurgical and ultrasonic instruments include multiple electronic components, e.g., nodes, that transmit digital communication signals therebetween. Some digital electronic communication nodes utilize of a single wire interface for the purpose of minimizing the required device electrical connections for transmitting data. In the single wire interface the transmission of data is half-duplex, meaning at any given instant of time a device can be either transmitting or receiving data, but not transmitting and receiving data simultaneously. Devices within these nodes that utilize single wire communication often have built in hardware and software drivers for aggregating the transmission and reception of data in this manner. Data coded on the single wire is dependent on its voltage relationship to the power supply for the device. Differential signaling uses two separate but complimentary signals where the data coded in those signals depends on their relationship to each other, and is not dependent on relationship to the power supply for the devices. This is commonly referred to as a differential bus. Where relatively long, and/or electrical noise susceptible links between communicating nodes exist, a differential bus provides improved immunity and higher fidelity transmission of digital signals. Nodes that participate on a differential bus are capable of handling both transmission and reception of data on the differential bus. This may be done either through separate differential busses for transmitting and receiving, or with added hardware or software-generated logic, to control the node for transmitting or receiving over a single differential bus.

A problem exists where nodes only have single-wire communication capability but are in an environment where differential media would provide for more reliable communication between the nodes. The communication link between the nodes is called the bus. The present disclosure provides a communication bus in which a single wire device sends temporal bitwise data as either dominant or passive to represent binary states on the bus. In the dominant state, the device puts the bus in a state that the bus cannot be changed by other devices; and in passive state, the bus can be changed by other devices. In view of this state system, logic devices are used to detect the dominant or passive state and separate them into two channels, one for transmission and another for receiving signals, respectively. When the dominant state is detected, the transmit logic is driven to the same binary state, and the receiver logic buffer is disabled. Conversely, when the passive state is detected, the receiver logic buffer is enabled and the transmitter logic buffer is disabled, rendering the node passive on the communication interface.

As such, the logic detecting the dominant/passive state of the device derives a direction control indicator for data communication (i.e., a transmitting or receiving indication). The separated transmit and receive channels are then passed to differential transceiver operational amplifier electronics that convert the signals to a differential bus for the transmitter, and from a differential bus for the receiver. These may be separate differential buses or one shared differential bus. In the case of a shared bus, the previously mentioned derived direction control indicator is used to control the transceiver electronics for transmission, or reception from the shared differential bus. Lastly, placing this solution at multiple nodes on a differential transmission medium allows multiple single-wire capable nodes to communicate on a single differential bus medium.

As used herein, the term "distal" refers to the portion that is described which is further from a user, while the term "proximal" refers to the portion that is being described which is closer to a user. Further, any or all of the aspects described herein, to the extent consistent, may be used in conjunction with any or all of the other aspects described herein.

Provided in accordance with aspects of the present disclosure is a single wire digital communication system including a first transmitter logic buffer and a first receiver logic buffer operably coupled to a first single wire device via a first single wire communication bus. The single wire digital communication system further includes a first differential transceiver operational amplifier and a second differential transceiver operational amplifier. The first differential transceiver operational amplifier is operably coupled to the first transmitter logic buffer via a first transmitter signal line and operably coupled to the first receiver logic buffer via a first receiver signal line. The second differential transceiver operational amplifier is operably coupled to the first differential transceiver operational amplifier via at least one differential bus. The single wire digital communication system further includes a second single wire device operably coupled to the differential bus and configured to communicate with the first single wire device.

In an aspect, the at least one differential bus is a single shared differential bus. Alternatively, the at least one differential bus may include a first differential bus and a second differential bus.

In an aspect, each of the first transmitter logic buffer and the first receiver logic buffer is a tri-state buffer.

In an aspect, the first transmitter signal line is configured to transmit a transmitter signal from an output of the first transmitter logic buffer through the first differential transceiver operational amplifier to an input of the first transmitter logic buffer and an inverted input of the first receiver logic buffer.

In an aspect, the first receiver signal line is operably coupled to an output of the first differential transceiver operational amplifier, an input of the first receiver logic buffer, and an input of the first transmitter logic buffer.

In an aspect, the single wire digital communication system includes a second transmitter logic buffer operably coupled to the second differential transceiver operational amplifier via a second transmitter signal line, a second receiver logic buffer operably coupled to the second differential transceiver operational amplifier via a second receiver signal line, and second single wire communication bus operably coupling the second single wire device to the second transmitter logic buffer and the second receiver logic buffer. The second transmitter signal line may be configured to transmit a transmitter signal from an output of the second transmitter logic buffer through the second differential transceiver operational amplifier to an input of the second transmitter logic buffer and an inverted input of the second receiver logic buffer. Additionally, or alternatively, the second receiver signal line may be operably coupled to an output of the second differential transceiver operational amplifier, an input of the second receiver logic buffer, and an input of the second transmitter logic buffer.

In another aspect of the present disclosure, an ultrasonic surgical instrument includes a housing, an ultrasonic transducer assembly supported by the housing, and an elongated assembly extending distally from the housing. The elongated assembly includes a waveguide configured to engage the ultrasonic transducer assembly. The waveguide defines a blade at a distal end thereof. Ultrasonic energy produced by the ultrasonic transducer assembly is transmitted along the waveguide to the blade for treating tissue adjacent the blade. The ultrasonic surgical instrument further includes a single wire digital communication system configured to control communication between a first single wire device disposed within the housing and a second single wire device disposed external the housing. The single wire digital communication system includes a first transmitter logic buffer and a first receiver logic buffer operably coupled to a first single wire device via a first single wire communication bus. The single wire digital communication system further includes a first differential transceiver operational amplifier and a second differential transceiver operational amplifier. The first differential transceiver operational amplifier is operably coupled to the first transmitter logic buffer via a first transmitter signal line and operably coupled to the first receiver logic buffer via a first receiver signal line. The second differential transceiver operational amplifier is operably coupled to the first differential transceiver operational amplifier via at least one differential bus. The single wire digital communication system further includes a second single wire device operably coupled to the differential bus and configured to communicate with the first single wire device.

In an aspect, the at least one differential bus is a single shared differential bus. Alternatively, the at least one differential bus may include a first differential bus and a second differential bus.

In an aspect, each of the first transmitter logic buffer and the first receiver logic buffer is a tri-state buffer.

In an aspect, the first transmitter signal line is configured to transmit a transmitter signal from an output of the first transmitter logic buffer through the first differential transceiver operational amplifier to an input of the first transmitter logic buffer and an inverted input of the first receiver logic buffer.

In an aspect, the first receiver signal line is operably coupled to an output of the first differential transceiver operational amplifier, an input of the first receiver logic buffer, and an input of the first transmitter logic buffer.

In an aspect, the single wire digital communication system includes a second transmitter logic buffer operably coupled to the second differential transceiver operational amplifier via a second transmitter signal line, a second receiver logic buffer operably coupled to the second differential transceiver operational amplifier via a second receiver signal line, and second single wire communication bus operably coupling the second single wire device to the second transmitter logic buffer and the second receiver logic buffer. The second transmitter signal line may be configured to transmit a transmitter signal from an output of the second transmitter logic buffer through the second differential transceiver operational amplifier to an input of the second transmitter logic buffer and an inverted input of the second receiver logic buffer. Additionally, or alternatively, the second receiver signal line may be operably coupled to an output of the second differential transceiver operational amplifier, an input of the second receiver logic buffer, and an input of the second transmitter logic buffer.

In another aspect of the present disclosure, a method for single wire digital communication in an ultrasonic surgical instrument includes detecting whether a bus including receiver logic buffer and transmitter logic buffer is in a dominant state or a passive state based on temporal bitwise data, disabling the receiver logic buffer and enabling the transmitter logic buffer, when the bus is detected to be in the dominant state, enabling the receiver logic buffer and disabling the transmitter logic buffer, when the bus is detected to be in the passive state, converting a signal from the transmitter logic buffer to a differential bus, converting a signal from the differential bus to a receiver, and transmitting a signal from the receiver to a single wire device via a single wire communication bus.

In an aspect, the differential bus includes a first bus configured to receive the signal from the transmitter logic buffer and a second bus configured to transmit a signal to the receiver.

In an aspect, the differential bus receives the signal from the transmitter logic buffer and transmits a signal to the receiver.

In an aspect, the method further includes controlling transceiver electronics configured to transmit the signal to the differential bus.

In an aspect, the method further includes controlling transceiver electronics configured to receive the signal from the differential bus.

BRIEF DESCRIPTION OF DRAWINGS

The above and other aspects and features of the present disclosure will become more apparent in light of the following detailed description when taken in conjunction with the accompanying drawings wherein like reference numerals identify similar or identical elements.

DETAILED DESCRIPTION

Figure 1:
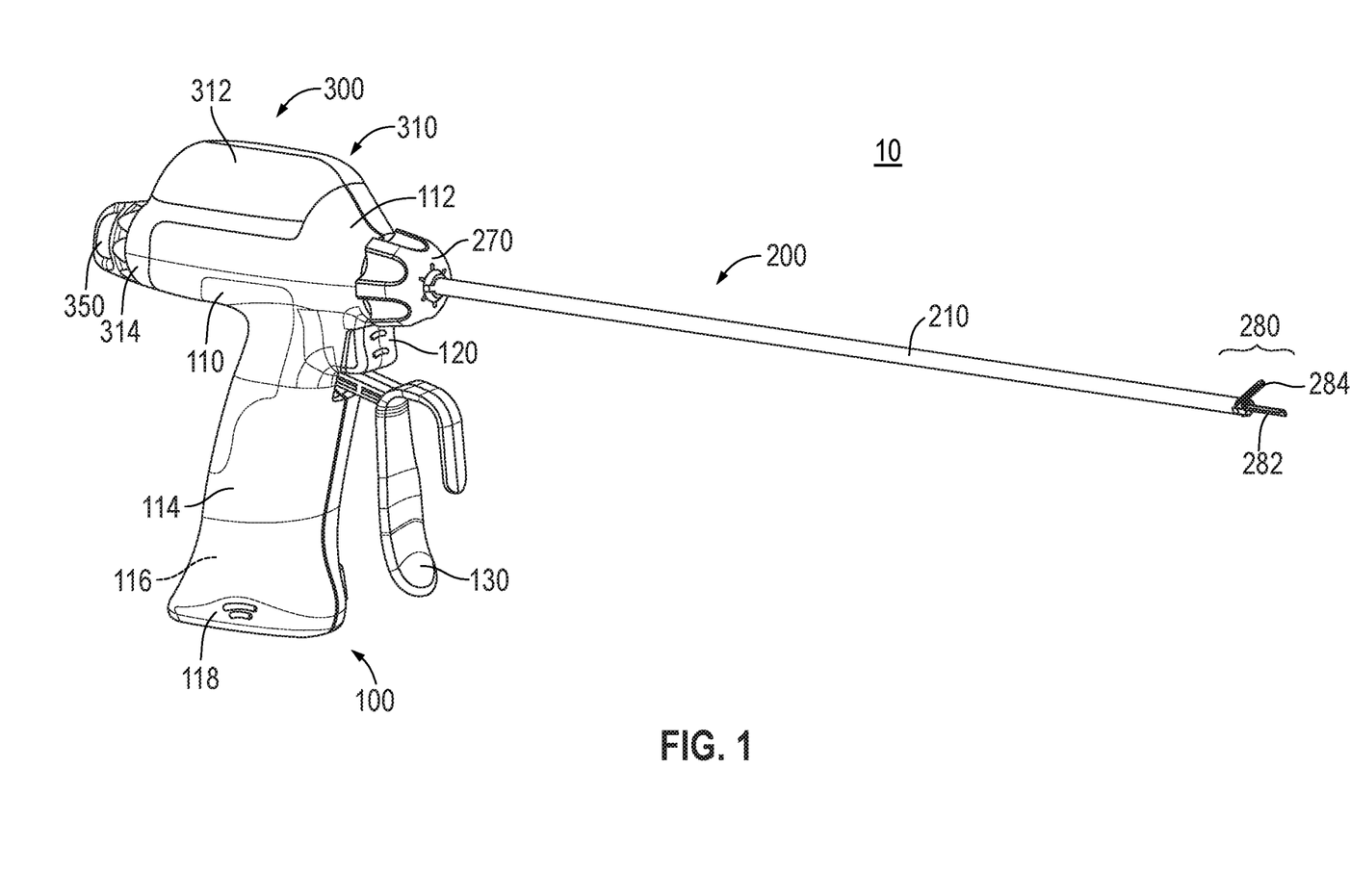
FIG. 1 is a side, perspective view of an ultrasonic surgical instrument provided in accordance with the present disclosure.
Figure 2:
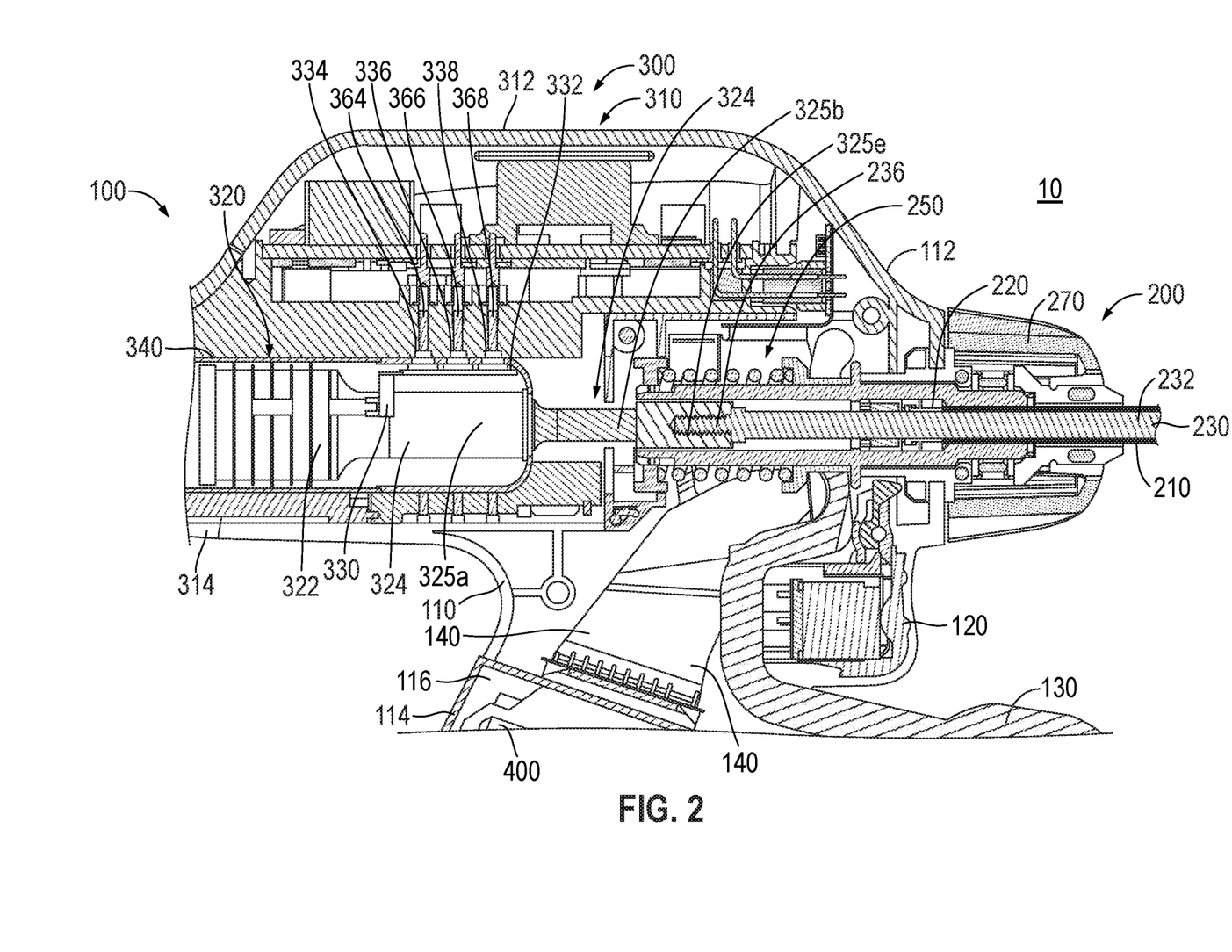
FIG. 2 is an enlarged, side, longitudinal, cross-sectional view of a proximal portion of the ultrasonic surgical instrument of FIG. 1.

Referring to FIGS. 1 and 2, an ultrasonic surgical instrument provided in accordance with the present disclosure is shown generally identified by reference numeral 10. Ultrasonic surgical instrument 10 includes a handle assembly 100 and an elongated assembly 200 extending distally from handle assembly 100. Handle assembly 100 includes a housing 110 defining a body portion 112 and a fixed handle portion 114. Handle assembly 100 further includes an activation button 120 and a clamp trigger 130.

Body portion 112 of housing 110 is configured to support an ultrasonic transducer and generator assembly ("TAG") 300 including a generator assembly 310 and an ultrasonic transducer assembly 320. TAG 300 may be permanently engaged with body portion 112 of housing 110 or removable therefrom. Generator assembly 310 includes a housing 312 configured to house the internal electronics of generator assembly 310, and a cradle 314 configured to rotatably support ultrasonic transducer assembly 320. Alternatively, generator assembly 310 may be remotely disposed and coupled to ultrasonic surgical instrument 10 by way of a surgical cable. TAG 300 is described in greater detail below.

Fixed handle portion 114 of housing 110 defines a compartment 116 configured to receive a battery assembly 400 and a door 118 configured to enclose compartment 116. An electrical connection assembly 140 is disposed within housing 110 of handle assembly 100 and serves to electrically couple activation button 120, generator assembly 310 of TAG 300, and battery assembly 400 with one another when TAG 300 is supported on or in body portion 112 of housing 110 and battery assembly 400 is disposed within compartment 116 of fixed handle portion 114 of housing 110, thus enabling activation of ultrasonic surgical instrument 10 in response to depression of activation button 120. In embodiments where generator assembly 310 is remote from ultrasonic surgical instrument 10, battery assembly 400 and the configuration of fixed handle portion 114 for receiving battery assembly 400 need not be provided, as generator assembly 310 may be powered by a standard wall outlet or other power source.

Referring still to FIGS. 1 and 2, elongated assembly 200 of ultrasonic surgical instrument 10 includes an outer drive sleeve 210, an inner support sleeve 220 disposed within outer drive sleeve 210, a waveguide 230 extending through inner support sleeve 220, a drive assembly 250, a rotation knob 270, and an end effector 280 including a blade 282 and a jaw 284. A proximal portion of outer drive sleeve 210 is operably coupled to clamp trigger 130 of handle assembly 100 via drive assembly 250, while a distal portion of outer drive sleeve 210 is operably coupled to jaw 284. As such, clamp trigger 130 is selectively actuatable to thereby move outer drive sleeve 210 about inner support sleeve 220 to pivot jaw 284 relative to blade 282 of end effector 280 from a spaced-apart position to an approximated position for clamping tissue between jaw 284 and blade 282. Drive assembly 250 provides a force-limiting feature whereby the clamping pressure applied to tissue is limited to a particular clamping pressure or particular clamping pressure range. Rotation knob 270 is rotatable in either direction to rotate elongated assembly 200 in either direction relative to handle assembly 100.

Waveguide 230 extends through inner support sleeve 220. Waveguide 230 defines a body 232 and a blade 282 extending from the distal end of body 232. Blade 282 serves as the blade of end effector 280. Waveguide 230 further includes a proximal threaded male connector 236 configured for threaded engagement within threaded female receiver 325e of nose 325b of ultrasonic horn 324 of ultrasonic transducer assembly 320 such that ultrasonic vibrations produced by ultrasonic transducer assembly 320 are transmitted along waveguide 230 to blade 282 for treating tissue clamping between blade 282 and jaw 284 or positioned adjacent to blade 282.

Figure 3:
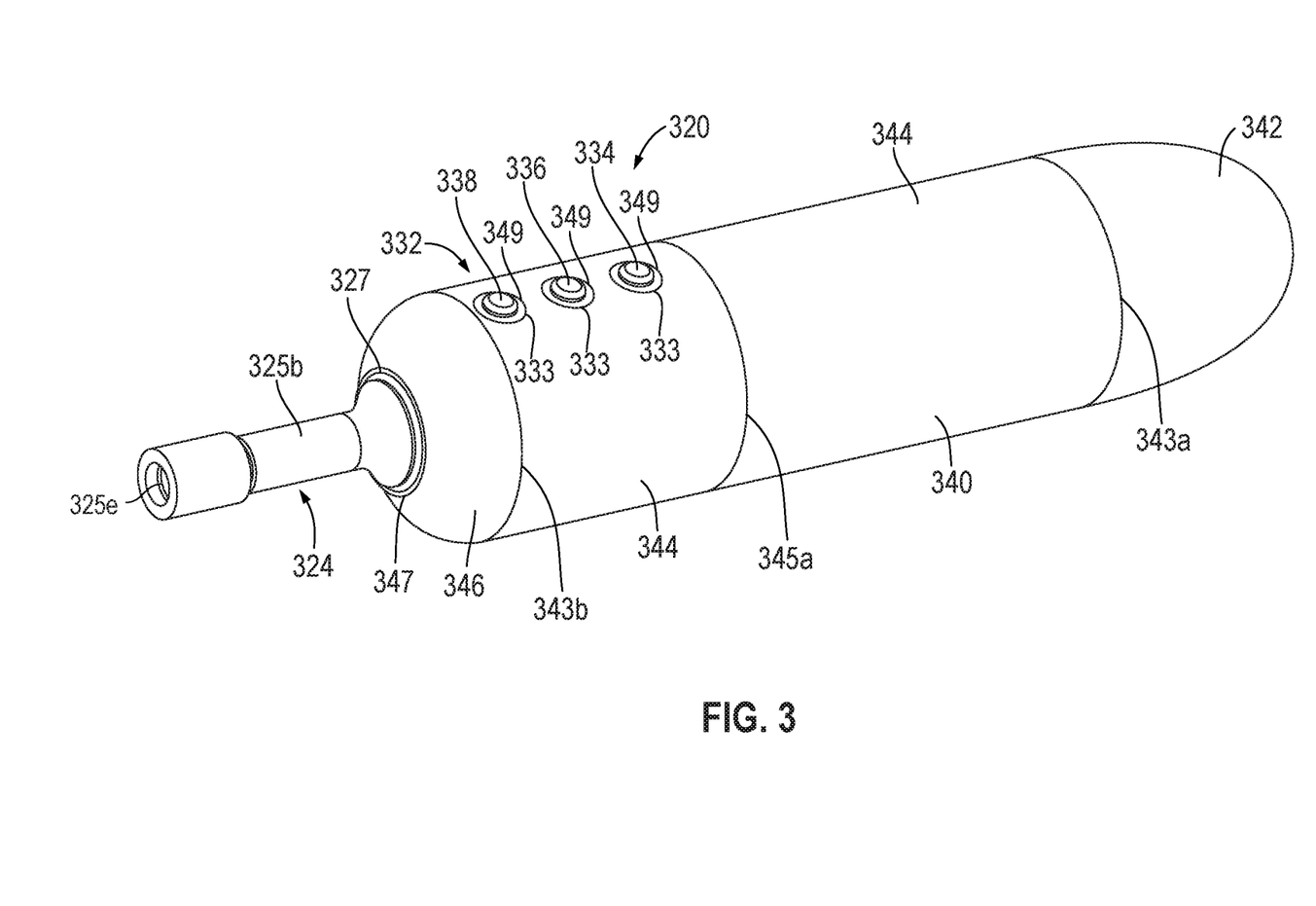
FIG. 3 is an enlarged, front, perspective view of the transducer assembly of the ultrasonic surgical instrument of FIG. 1.
Figure 4:
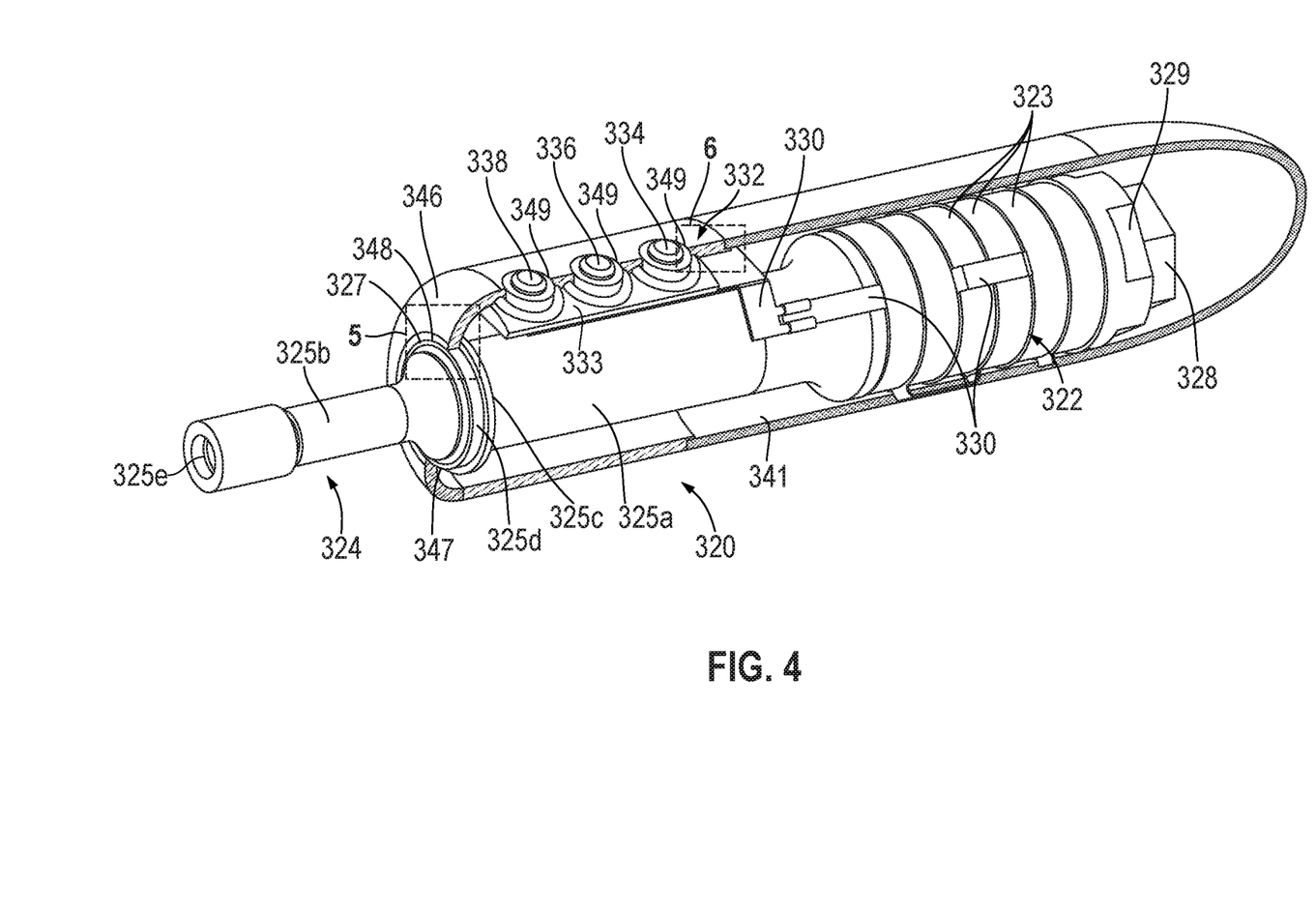
FIG. 4 is an enlarged, front, perspective view of the transducer assembly of the ultrasonic surgical instrument of FIG. 1 with a portion of the casing removed to illustrate the internal features and components thereof.

Referring to FIGS. 2-4, ultrasonic transducer assembly 320 includes a piezoelectric stack 322, an ultrasonic horn 324, a bolt 328 (FIG. 4), a proximal nut 329 (FIG. 4), first and second electrode assemblies 330, a contact assembly 332, and a casing 340. Bolt 328 secures piezoelectric stack 322 between ultrasonic horn 324 and a proximal nut 329. First and second electrode assemblies 330 are interdisposed between the piezoelectric elements 323 of piezoelectric stack 322 and connect to contact assembly 332. Contact assembly 332 enables communication of drive and/or data signals through casing 340, e.g., between piezoelectric stack 322 and generator assembly 310. Casing 340, together with ultrasonic horn 324, defines a hermetically sealed enclosure having an interior 341 that houses piezoelectric stack 322, a portion of ultrasonic horn 324, bolt 328, proximal nut 329, first and second electrode assemblies 330, and a portion of contact assembly 332.

Ultrasonic transducer assembly 320 further includes a rotation knob 350 (FIG. 1) mounted on or formed with casing 340 at the proximal end of casing 340. Rotation knob 350 is accessible from the exterior of handle assembly 100 and is configured for manual rotation to rotate ultrasonic transducer assembly 320 relative to generator assembly 310 and housing 110.

Continuing with reference to FIGS. 1 and 2, generator assembly 310 includes a plurality of ring contacts 364, 366, 368 surrounding ultrasonic transducer assembly 320 and disposed in slidable contact with corresponding slip contacts 334, 336, 338, respectively, of contact assembly 332 of ultrasonic transducer assembly 320. Thus, ring contacts 364, 366, 368 and respective slip contacts 334, 336, 338 define slip ring contact assemblies that enable drive and/or data signals to be communicated between generator assembly 310 and piezoelectric stack 322 of ultrasonic transducer assembly 320 regardless of the rotational orientation of ultrasonic transducer assembly 320 relative to generator assembly 310. More specifically, with respect to drive signal communication, the first of the electrode assemblies 330 includes at least one positive electrode disposed between the piezoelectric elements 323 of piezoelectric stack 322 and an electrode connector connecting the at least one positive electrode with slip contact 334 which, in turn, is disposed in contact with ring contact 364. The second of the electrode assemblies 330 includes at least one negative electrode disposed between the piezoelectric elements 323 of piezoelectric stack 322 and an electrode connector connecting the at least one negative electrode with slip contact 336 which, in turn, is disposed in contact with ring contact 366. As such, a drive signal voltage may be applied from generator assembly 310 across the piezoelectric elements 323 of the piezoelectric stack 322 via the positive and negative electrodes. The piezoelectric stack 322, in turn, converts the applied voltage into mechanical energy, in the form of ultrasonic vibrations, that is transmitted to ultrasonic horn 324. In other embodiments, the second of the electrode assemblies 330 is omitted and casing 340 is utilized as the negative electrode for piezoelectric stack 322.

With respect to data signal communication, contact assembly 332 may include a data storage and processing device (not explicitly shown) (or electrical connectors, with the data storage and processing device disposed within generator assembly 310) disposed in communication with ultrasonic horn 324 (and/or other portions of ultrasonic transducer assembly 320). The data storage and processing device, more specifically, may be a microprocessor chip or other suitable chip with sensory circuitry to detect various conditions, parameters, properties, etc. of piezoelectric stack 322, ultrasonic horn 324, and/or other portions of ultrasonic transducer assembly 320. The data storage and processing device may be configured to sense, for example, a frequency, amplitude, impedance, and/or temperature of ultrasonic horn 324 (or other portion of ultrasonic transducer assembly 320); the number of times ultrasonic transducer assembly 320 has been activated, the duration of activation ultrasonic transducer assembly 320, etc. The data storage and processing device may additionally or alternatively include a memory storing information relating to ultrasonic transducer assembly 320 such as, for example, model, serial number, manufacture date, calibration and/or testing information, manufacturer setting information, etc. In embodiments where the data storage and processing device includes sensor circuitry, the memory may also store the sensed data.

The data storage and processing device (or electrical connectors) within ultrasonic transducer assembly 320 are coupled to slip contact 338 of contact assembly 332 which, in turn, is disposed in contact with ring contact 368 to enable communication of data signals between ultrasonic transducer assembly 320 and ultrasonic generator assembly 310.

Ultrasonic horn 324 includes a body 325a disposed within casing 340 of ultrasonic transducer assembly 320 and a nose 325b extending distally from body 325a externally of casing 340 of ultrasonic transducer assembly 320. A proximal collar 325c is disposed between body 325a and nose 325b and an annular, outwardly-facing contact surface 325d is disposed distally adjacent proximal collar 325c to facilitate formation of a hermetic seal between casing 340 and ultrasonic horn 324, as detailed below. Annular, outwardly-facing contact surface 325d may be disposed at or near a nodal point along ultrasonic horn 324. Nose 325b of ultrasonic horn 324 defines a distal threaded female receiver 325e configured to enable releasable threaded engagement of waveguide 230 with ultrasonic horn 324. Ultrasonic horn 324 may be formed from a metal, e.g., titanium, aluminum, stainless steel, an amorphous metal, etc., or other suitable material(s).

Referring to FIGS. 3-6, casing 340 of ultrasonic transducer assembly 320, as noted above, defines a hermetically sealed enclosure having an interior 341 that houses piezoelectric stack 322, a portion of ultrasonic horn 324, bolt 328, proximal nut 329, first and second electrode assemblies 330, and a portion of contact assembly 332. Casing 340 may be formed from a metal, e.g., titanium, aluminum, stainless steel, an amorphous metal, etc., or other suitable material(s). Casing 340 may be formed from a plurality of casing components including, for example, a proximal cap portion 342, one or more intermediate tube portions 344, and a distal cap portion 346. Proximal cap portion 342 defines a closed proximal end and an open distal end, the intermediate tube portion(s) 344 defines open proximal and distal ends, and distal cap portion 346 defines an open proximal end and a reduced-diameter opening 347 at the distal end thereof. Distal cap portion 346 further defines an annular, inwardly-facing contact surface 348 surrounding the reduced-diameter opening 347. Casing 340 further includes one or more windows 349 defined therethrough for sealing receipt of contact assembly 332 therein, as detailed below.

The distal end of proximal cap portion 342 and the proximal end of the proximal-most intermediate tube portion 344 abut one another to define a joint 343a and are welded to one another annularly about joint 343a to secure and hermetically seal the distal end of proximal cap portion 342 and the proximal end of the proximal-most intermediate tube portion 344 with one another. One of the distal end of proximal cap portion 342 or the proximal end of the proximal-most intermediate tube portion 344 includes a flange (not explicitly shown, see flange 345b (FIG. 6)) overlapping, on the interior side thereof, joint 343a. By overlapping joint 343a, the flange protects the interior 341 of casing 340 (and any components disposed therein) as joint 343a is welded to secure and hermetically seal the distal end of proximal cap portion 342 and the proximal end of the proximal-most intermediate tube portion 344 with one another. As an alternative to welding, other suitable methods of securing and hermetically sealing the distal end of proximal cap portion 342 and the proximal end of the proximal-most intermediate tube portion 344 are also contemplated such as, for example, press-fitting, using O-rings, adhesion, etc.

The distal end of the distal-most intermediate tube portion 344 and the proximal end of distal cap portion 346 abut one another to define a joint 343b and are welded to one another annularly about joint 343b to secure and hermetically seal the distal end of the distal-most intermediate tube portion 344 and the proximal end of distal cap portion 346 with one another. One of the distal end of the distal-most intermediate tube portion 344 or the proximal end of distal cap portion 346 includes a flange (not explicitly shown, see flange 345b (FIG. 6)) overlapping, on the interior side thereof, joint 343b to protect the interior 341 of casing 340 as joint 343b is welded to secure and hermetically seal the distal end of the distal-most intermediate tube portion 344 and the proximal end of distal cap portion 346 with one another.

Figure 6:
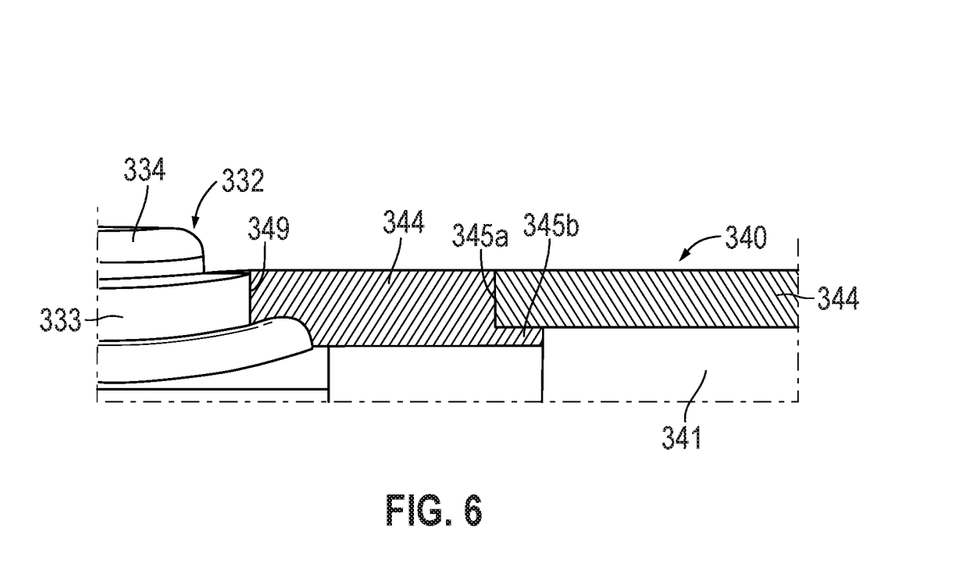
FIG. 6 is an enlarged, side view of the area of detail indicated as "6" in FIG. 4.

Turning to FIG. 6, in embodiments where multiple intermediate tube portions 344 are provide, the abutting ends of adjacent intermediate tube portions 344 may be welded to one another similarly as detailed above, e.g., with a flange 345*b* overlapping the weld joint 345*a* on the interior side thereof. As an alternative to including proximal, intermediate, and distal portions 342, 344, 346, respectively, welded to one another about annular joints, casing 340 may include, for example, left and right half portions welded to one another along a longitudinal joint, or may include any suitable combination of components welded to one another via annular and/or longitudinal joints (and including annular and/or longitudinal internal flanges). In other embodiments, casing 340 is formed as a single, monolithic piece of material.

Figure 5:
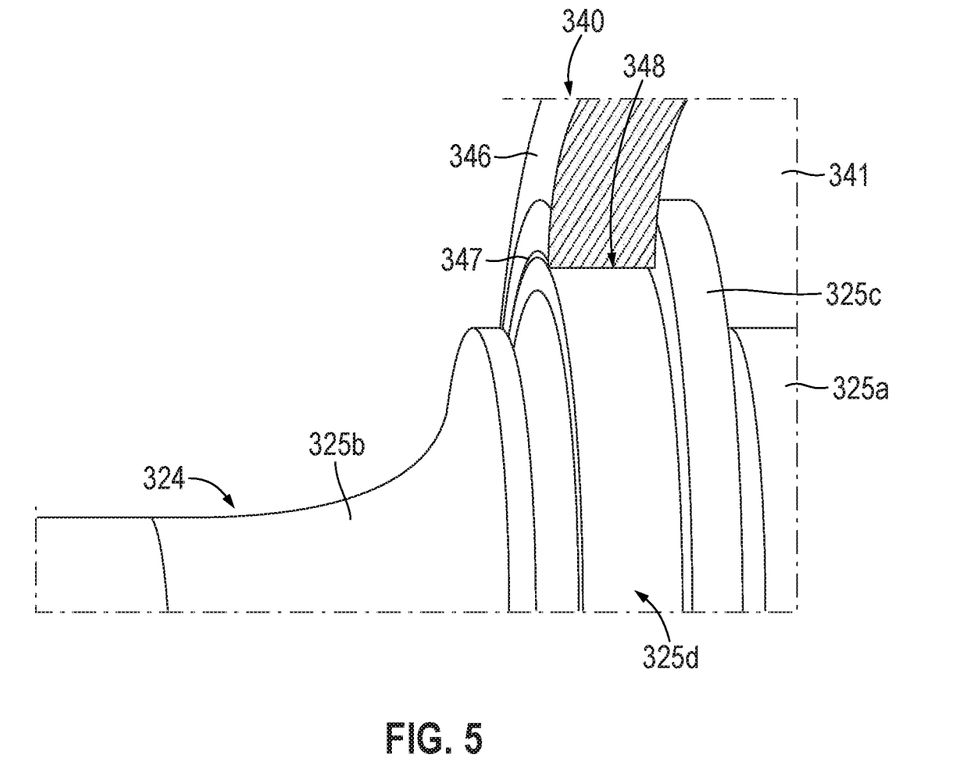
FIG. 5 is an enlarged, perspective view of the area of detail indicated as "5" in FIG. 4.

With particular reference back to FIG. 5, in order to fully enclose and hermetically seal interior 341 of casing 340, thus hermetically sealing piezoelectric stack 322, a portion of ultrasonic horn 324, bolt 328, proximal nut 329, first and second electrode assemblies 330, and a portion of contact assembly 332 within casing 340, distal cap portion 346 of casing 340 is positioned such that ultrasonic horn 324 extends through reduced-diameter opening 347. More specifically, casing 340 and ultrasonic horn 324 are positioned such that ultrasonic horn 324 extends through reduced-diameter opening 347 with proximal collar 325*c* abutting the interior surface of casing 340 adjacent reduced-diameter opening 347 and such that outwardly-facing contact surface 325*d* and inwardly-facing contact surface 348 abut one another to define a joint 327. Distal cap portion 346 of casing 340 and ultrasonic horn 324 are welded to one another annularly about joint 327 to secure and hermetically seal the distal end of distal cap portion 346 and ultrasonic horn 324 with one another. Proximal collar 325*c* overlaps joint 327, on the interior side thereof, to thereby protect the interior 341 of casing 340 (and any components disposed therein) as joint 327 is welded to secure and hermetically seal distal cap portion 346 of casing 340 and ultrasonic horn 324 with one another. As noted above, annular, outwardly-facing contact surface 325*d* of ultrasonic horn 324 may be disposed at a nodal point along ultrasonic horn 324 and, thus, joint 327 (where casing 340 is attached to ultrasonic horn 324) is likewise disposed at a nodal point along ultrasonic horn 324 such that casing 340 remains ultrasonically inert.

Referring to FIGS. 2 and 4, contact assembly 332, as noted above, includes slip contacts 334, 336, 338 extending from interior 341 of casing 340 to the exterior thereof. More specifically, contacts 334, 336, 338 protrude radially outwardly beyond the exterior surface of casing 340 to enable slidable contact with corresponding ring contacts 364, 366, 368, respectively, of generator assembly 310 without casing 340 contacting ring contacts 364, 366, 368. Further, as casing 340 is formed from an electrically-conductive material, e.g., a metal, contact assembly 332 further includes an electrically-insulative frame 333 sealingly retaining contacts 334, 336, 338 therein in electrical isolation from one another and casing 340. Frame 333 may be formed from a polymer or other suitable electrically-insulative material and may be overmolded about contacts 334, 336, 338 to secure and form a hermetic seal thereabout, hermetically sealed and secured about contacts 334, 336, 338 using an epoxy or other seal, or may be hermetically sealed and secured about contacts 334, 336, 338 in any other suitable manner. Further, frame 333 may be overmolded within window(s) 349 of casing 340 to secure contact assembly 332 therein and form a hermetic seal therebetween (via the same overmold as that securing and sealing contacts 334, 336, 338 or an additional overmold), may be secured and hermetically sealed within window(s) 349 using an epoxy or other seal, or may be secured and hermetically sealed within window(s) 349 in any other suitable manner.

The above-detailed hermetic sealing of casing 340 to ultrasonic horn 324 (as well as hermetically sealing contact assembly 332 within window(s) 349 of casing 340) ensures that transducer assembly 320 is capable of withstanding multiple rounds of sterilization, e.g., autoclave sterilization.

Figure 7:
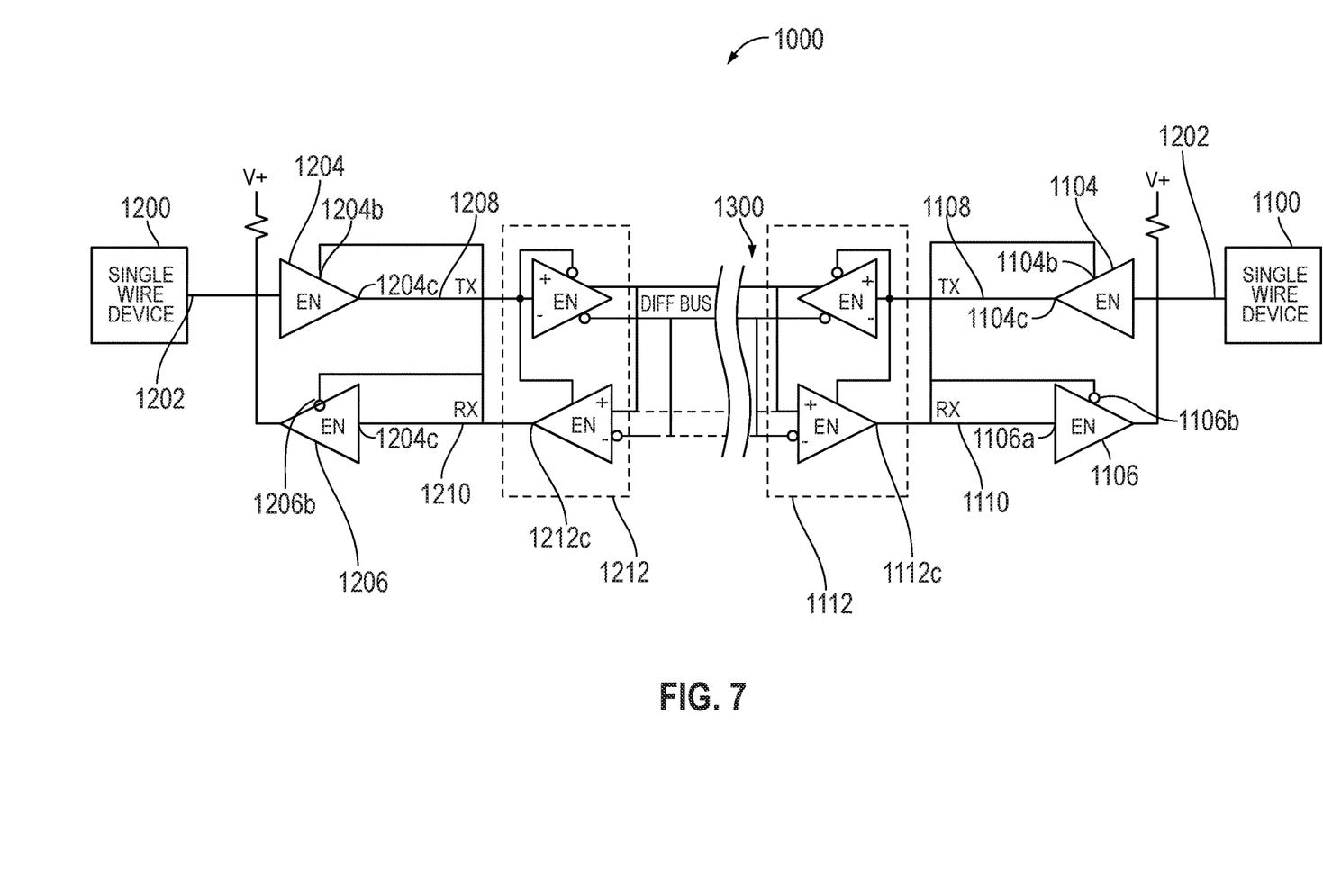
FIG. 7 is a circuit diagram of a single wire digital communication system of the ultrasonic surgical instrument provided in accordance with the present disclosure.

With reference to FIG. 7, a circuit diagram of a single wire digital communication system 1000 usable with single wire devices of an ultrasonic surgical instrument is illustrated. In embodiments, the single wire digital communication system 1000 may be used with any surgical instrument that utilizes a single wire bus for digital communication between various nodes. In an aspect, the first single wire device is disposed within the housing 110 of the handle assembly 100 and the second single wire device 1200 is disposed external to the housing 110, proximate the end effector 280. In aspects, either or both of the first single wire device 1100 or the second single wire device 1200 may include or may be coupled to sensors or data storage devices, and other integrated circuit components similar to those described above.

The presently disclosed single wire digital communication system 1000 can be read from the storage and processing devices and electronic components in the various components of the system and ultrasonic surgical instrument in an efficient manner. The presently disclosed communication protocol increases reliability because there are fewer mechanical parts subject to corrosion and/or failure, particularly where pins may be exposed to blood and other fluids.

The single wire digital communication system 1000 includes a communication bus in which a single wire device sends temporal bitwise data as either dominant or passive to represent binary states on the bus. In the dominant state, the device puts the bus in a state that the bus cannot be changed by other devices; and in passive state, the bus can be changed by other devices. In view of this state system, logic devices are used to detect the dominant or passive state and separate them into two channels, one for transmission and another for receiving signals, respectively. When the dominant state is detected, the transmit logic is driven to the same binary state, and the receiver logic buffer is disabled. Conversely, when the passive state is detected, the receiver logic buffer is enabled and the transmitter logic buffer is disabled, rendering the node passive on the communication interface.

As such, the logic detecting the dominant/passive state of the device derives a direction control indicator for data communication (i.e., a transmitting or receiving indication). The separated transmit and receive channels are then passed to differential transceiver operational amplifier electronics that convert the signals to a differential bus for the transmitter, and from a differential bus for the receiver. These may be separate differential buses or one shared differential bus. In the case of a shared bus, the previously mentioned derived direction control indicator is used to control the transceiver electronics for transmission, or reception from the shared differential bus. Lastly, placing this solution at multiple nodes on a differential transmission medium allows multiple single-wire capable nodes to communicate on a single differential bus medium.

With particular reference to FIG. 7, the single wire digital communication system 1000 includes a first single wire device 1100 and a second single wire device 1200 communicating with each other. The first single wire device 1100 may be coupled to a controller, or other suitable component, of an ultrasonic surgical instrument 10 (for example, within a housing of the ultrasonic surgical instrument 10) and the second single wire device 1200 may be coupled to another component of the ultrasonic surgical instrument 10 (e.g., a sensor (not shown) disposed on an end effector of the ultrasonic surgical instrument).

The single wire digital communication system 1000 includes first transmitter logic buffer 1104 and first receiver logic buffer 1106 operably coupled to a first single wire device 1100 via a first single wire communication bus 1102. The first transmitter logic buffer 1104 and the first receiver logic buffer 1106 may be a tri-state buffer or other suitable logic or non-logic switching device. The single wire digital communication system 1000 also includes a first differential transceiver operational amplifier 1112 operably coupled to the first transmitter logic buffer 1104 via a first transmitter signal line 1108 and operably coupled to the first receiver logic buffer 1106 via a first receiver signal line 1110. A second differential transceiver operational amplifier 1212 is operably coupled to the first differential transceiver operational amplifier 1112 via at least one differential bus 1300. A second single wire device 1200 is operably coupled to the differential bus 1300 and configured to communicate with the first single wire device 1100.

As described above, the differential bus 1300 may be a single shared differential bus or may include two separate differential busses. The first transmitter signal line 1108 is configured to transmit a transmitter signal from an output 1104c of the first transmitter logic buffer 1104 through the first differential transceiver operational amplifier 1112 to an input 1104b of the first transmitter logic buffer 1104 and an inverted input 1106b of the first receiver logic buffer 1106. The first receiver signal line 1110 is operably coupled to an output 1112c of the first differential transceiver operational amplifier 1112, an input 1106a of the first receiver logic buffer 1106, and an input 1104b of the first transmitter logic buffer 1104.

In an aspect, the single wire digital communication system 1000 further includes second transmitter logic buffer 1204 operably coupled to the second differential transceiver operational amplifier 1212 via a second transmitter signal line 1208. The single wire digital communication system 1000 also includes a second receiver logic buffer 1206 operably coupled to the second differential transceiver operational amplifier 1212 via a second receiver signal line 1210, and a second single wire communication bus 1202 operably coupling the second single wire device 1200 to the second transmitter logic buffer 1204 and the second receiver logic buffer 1206. The second transmitter signal line 1208 is configured to transmit a transmitter signal from an output 1204c of the second transmitter logic buffer 1204 through the second differential transceiver operational amplifier 1212 to an input 1204b of the second transmitter logic buffer 1204 and an inverted input 1206b of the second receiver logic buffer 1206. The second receiver signal line 1210 is operably coupled to an output 1212c of the second differential transceiver operational amplifier 1212, an input 1206a of the second receiver logic buffer 1206, and an input 1204b of the second transmitter logic buffer 1204.

The structure of the single wire digital communication system 1000 enables logic devices to detect a dominant or passive state, and separate the two into two channels of transmit (e.g., first transmitter signal line 1108 and second transmitter signal line 1208) and receive (for example, first receiver signal line 1110 and second receiver signal line 1210), respectively.

Figure 8:
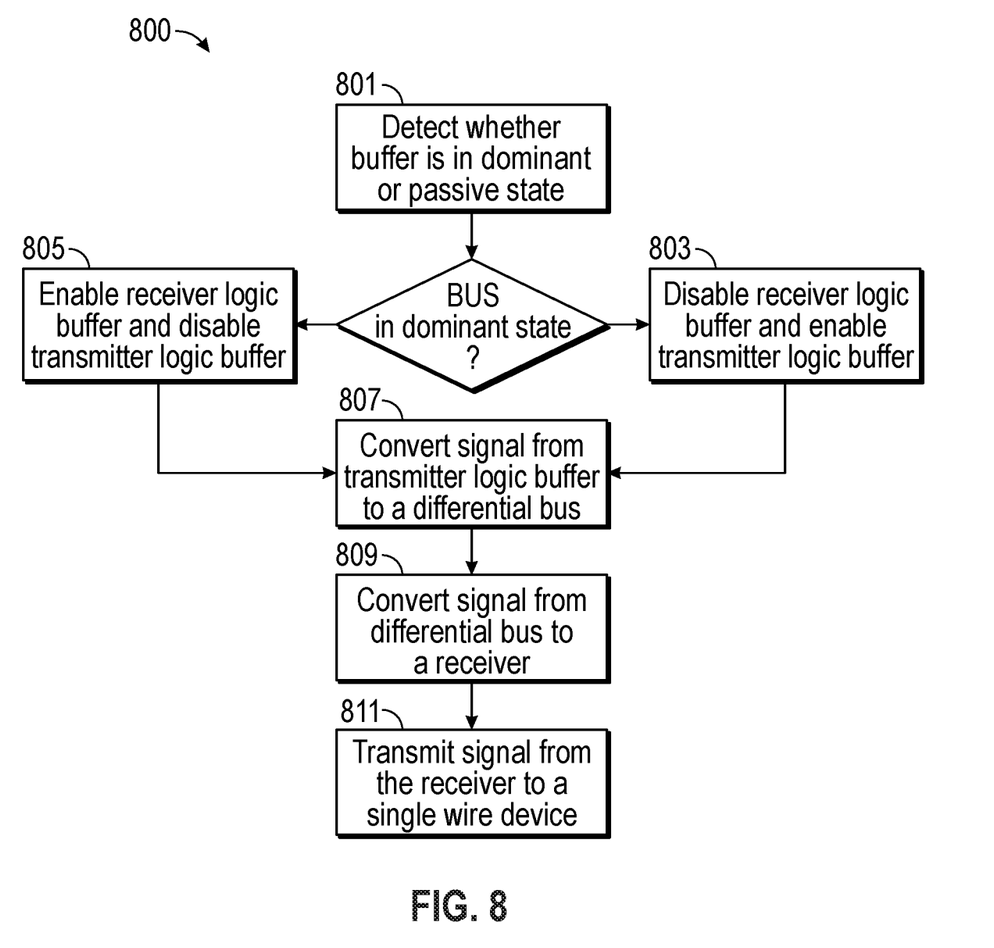
FIG. 8 is a flow chart illustrating a method for single wire digital communication in accordance with the present disclosure.

FIG. 8 illustrates a flow chart illustrating a method for single wire digital communication in accordance with the present disclosure, described as method 800. The method for single wire digital communication in an ultrasonic surgical instrument, for example, using single wire digital communication system 1000 (FIG. 7) includes detecting whether a bus including receiver logic buffer and transmitter logic buffer is in a dominant state or a passive state (step 801). The detection in step 801 may be based on temporal bitwise data. When the bus is in the dominant state, the bus cannot be changed by another device and when the bus is in the passive state, the bus can be changed by another device. When the bus is detected to be in the dominant state, the receiver logic buffer is disabled and the transmitter logic buffer is enabled (step 803). Alternatively, when the bus is detected to be in the passive state, the receiver logic buffer is enabled and the transmitter logic buffer is disabled (step 805).

The method also includes converting a signal from the transmitter logic buffer to a differential bus (step 807), converting a signal from a differential bus to a receiver (step 809), and transmitting a signal from the receiver to a single wire device via a single wire communication bus (step 811). In an aspect, the method includes controlling transceiver electronics for transmission to the same differential bus, and additionally may include controlling transceiver electronics for reception from the same differential bus. Converting the signal from the transmitter logic buffer to the differential bus may include passing the signal from the transmitter logic buffer through a differential transceiver operational amplifier. Additionally, or alternatively, converting the signal from the differential bus to the receiver includes passing the signal from the differential bus through a differential transceiver operational amplifier.

While several embodiments of the disclosure have been detailed above and are shown in the drawings, it is not intended that the disclosure be limited thereto, as it is intended that the disclosure be as broad in scope as the art will allow and that the specification be read likewise. Therefore, the above description and accompanying drawings should not be construed as limiting, but merely as exemplifications of particular embodiments. Those skilled in the art will envision other modifications within the scope and spirit of the claims appended hereto.

What is claimed is:

1. A single wire digital communication system comprising:
   a first transmitter logic buffer and a first receiver logic buffer operably coupled to a first single wire device via a first single wire communication bus;
   a first differential transceiver operational amplifier operably coupled to the first transmitter logic buffer via a first transmitter signal line and operably coupled to the first receiver logic buffer via a first receiver signal line;
   a second differential transceiver operational amplifier operably coupled to the first differential transceiver operational amplifier via at least one differential bus; and
   a second single wire device operably coupled to the differential bus and configured to communicate with the first single wire device, wherein the first transmitter signal line is configured to transmit a transmitter signal from an output of the first transmitter logic buffer to an input of the first transmitter logic buffer and an inverted input of the first receiver logic buffer.

2. The single wire digital communication system of claim 1, wherein the at least one differential bus is a single shared differential bus.

3. The single wire digital communication system of claim 1, wherein the at least one differential bus includes a first differential bus and a second differential bus.

4. The single wire digital communication system of claim 1, wherein each of the first transmitter logic buffer and the first receiver logic buffer is a tri-state buffer.

5. The single wire digital communication system of claim 1, wherein the first transmitter signal line is configured to transmit the transmitter signal from the output of the first transmitter logic buffer through the first differential transceiver operational amplifier.

6. The single wire digital communication system of claim 1, wherein the first receiver signal line is operably coupled to an output of the first differential transceiver operational amplifier, an input of the first receiver logic buffer, and the input of the first transmitter logic buffer.

7. The single wire digital communication system of claim 1, further comprising:
a second transmitter logic buffer operably coupled to the second differential transceiver operational amplifier via a second transmitter signal line;
a second receiver logic buffer operably coupled to the second differential transceiver operational amplifier via a second receiver signal line; and
a second single wire communication bus operably coupling the second single wire device to the second transmitter logic buffer and the second receiver logic buffer.

8. The single wire digital communication system of claim 7, wherein:
the second transmitter signal line is configured to transmit a transmitter signal from an output of the second transmitter logic buffer to an input of the second transmitter logic buffer and an inverted input of the second receiver logic buffer; and
the second receiver signal line is operably coupled to an output of the second differential transceiver operational amplifier, a second input of the second receiver logic buffer, and the input of the second transmitter logic buffer.

9. An ultrasonic surgical instrument, comprising:
a housing;
an ultrasonic transducer assembly supported by the housing;
an elongated assembly extending distally from the housing, the elongated assembly including a waveguide configured to engage the ultrasonic transducer assembly, the waveguide defining a blade at a distal end thereof, wherein ultrasonic energy produced by the ultrasonic transducer assembly is transmitted along the waveguide to the blade for treating tissue adjacent the blade; and
a single wire digital communication system configured to control communication between a first single wire device disposed within the housing and a second single wire device disposed external the housing, the single wire digital communication system comprising:
a first transmitter logic buffer and a first receiver logic buffer operably coupled to a first single wire device via a first single wire communication bus;
a first differential transceiver operational amplifier operably coupled to the first transmitter logic buffer via a first transmitter signal line and operably coupled to the first receiver logic buffer via a first receiver signal line;
a second differential transceiver operational amplifier operably coupled to the first differential transceiver operational amplifier via at least one differential bus; and
a second single wire device operably coupled to the differential bus and configured to communicate with the first single wire device, wherein the first transmitter signal line is configured to transmit a transmitter signal from an output of the first transmitter logic buffer to an input of the first transmitter logic buffer and an inverted input of the first receiver logic buffer.

10. The ultrasonic surgical instrument according to claim 9, wherein the at least one differential bus is a single shared differential bus.

11. The ultrasonic surgical instrument according to claim 9, wherein the at least one differential bus includes a first differential bus and a second differential bus.

12. The ultrasonic surgical instrument according to claim 9, wherein each of the first transmitter logic buffer and the first receiver logic buffer is a tri-state buffer.

13. The ultrasonic surgical instrument according to claim 9, wherein the first transmitter signal line is configured to transmit the transmitter signal from the output of the first transmitter logic buffer through the first differential transceiver operational amplifier.

14. The ultrasonic surgical instrument according to claim 9, wherein the first receiver signal line is operably coupled to an output of the first differential transceiver operational amplifier, an input of the first receiver logic buffer, and the input of the first transmitter logic buffer.

15. The ultrasonic surgical instrument according to claim 9, wherein the single wire digital communication system further comprises:
a second transmitter logic buffer operably coupled to the second differential transceiver operational amplifier via a second transmitter signal line;
a second receiver logic buffer operably coupled to the second differential transceiver operational amplifier via a second receiver signal line; and
a second single wire communication bus operably coupling the second single wire device to the second transmitter logic buffer and the second receiver logic buffer.

16. A method for single wire digital communication in an ultrasonic surgical instrument, the method comprising:
detecting whether a bus including a receiver logic buffer and a transmitter logic buffer is in a dominant state or a passive state based on temporal bitwise data;
disabling the receiver logic buffer and enabling the transmitter logic buffer, when the bus is detected to be in the dominant state by transmitting a transmitter signal from an output of the transmitter logic buffer to an input of the transmitter logic buffer and an inverted input of the receiver logic buffer;
enabling the receiver logic buffer and disabling the transmitter logic buffer, when the bus is detected to be in the passive state;
converting a signal from the transmitter logic buffer to a differential bus;
converting a signal from the differential bus to a receiver; and
transmitting a signal from the receiver to a single wire device via a single wire communication bus.

17. The method of claim 16, wherein the differential bus includes a first bus configured to receive the signal from the transmitter logic buffer and a second bus configured to transmit a signal to the receiver.

18. The method of claim 16, wherein the differential bus receives the signal from the transmitter logic buffer and transmits a signal to the receiver.

19. The method of claim 18, further comprising controlling transceiver electronics configured to transmit the signal to the differential bus.

20. The method of claim 18, further comprising controlling transceiver electronics configured to receive the signal from the differential bus.

* * * * *